(12) United States Patent
Tickner et al.

(10) Patent No.: US 9,528,951 B2
(45) Date of Patent: Dec. 27, 2016

(54) METHOD FOR RAPID ANALYSIS OF GOLD

(71) Applicant: COMMONWEALTH SCIENTIFIC AND INDUSTRIAL RESEARCH ORGANISATION, Campbell, Australian Capital Territory (AU)

(72) Inventors: James Tickner, Campbell (AU); Greg Roach, Campbell (AU)

(73) Assignee: COMMONWEALTH SCIENTIFIC AND INDUSTRIAL RESEARCH ORGANISATION, Campbell, Australian Capital Territory ( * ) Notice: Subject to any disclaimer, the term of this patent is extended or adjusted under 35 U.S.C. 154(b) by 0 days.

(21) Appl. No.: 15/104,279

(22) PCT Filed: Dec. 16, 2014

(86) PCT No.: PCT/AU2014/050424
§ 371 (c)(1),
(2) Date: Jun. 14, 2016

(87) PCT Pub. No.: WO2015/089580
PCT Pub. Date: Jun. 25, 2015

(65) Prior Publication Data
US 2016/0320321 A1    Nov. 3, 2016

(30) Foreign Application Priority Data
Dec. 18, 2013 (GB) .................................. 1322365.6

(51) Int. Cl.
G01N 23/221 (2006.01)
G01N 23/22 (2006.01)
A61B 6/00 (2006.01)

(52) U.S. Cl.
CPC ........ G01N 23/221 (2013.01); G01N 23/2208 (2013.01); A61B 6/4258 (2013.01);
(Continued)

(58) Field of Classification Search
CPC ...... G01N 23/00; G01N 23/22; G01N 23/221; G01N 23/2076; G01N 23/223; G01N 33/00; G01N 33/20; G01N 35/00; G01N 35/00584; G01N 35/00594; G01N 35/00693; G01N 2203/0003; G01N 2223/00; G01N 2223/07; G01N 2223/074; G01N 2223/076; G01N 2223/0763; G01N 2223/10; G01N 2223/101; G01N 2223/1013; G01N 2223/1016; G01N 2223/20; G01N 2223/203; G01N 2223/303; G01N 2223/3037; G01N 2223/60; G01T 1/00; G01T 1/16; G01T 1/18; G01T 1/36; G01T 1/362; G01T 1/366; G01T 1/38; G01T 7/00; G01T 7/005; A61B 6/00; A61B 6/4092; A61B 6/42; A61B 6/4208; A61B 6/4258; A61B 6/48; A61B 6/485
See application file for complete search history.

(56) References Cited

U.S. PATENT DOCUMENTS 3,965,353 A * 6/1976 Macovski ................ A61B 6/02
250/366
5,293,414 A * 3/1994 Ettinger ............... G01V 5/0025
376/157
(Continued)

FOREIGN PATENT DOCUMENTS

CS   8808966 A   10/1991
GB   1070337    6/1967
(Continued)

OTHER PUBLICATIONS

Grodzov, D.S., et al., "Computation of Correction Coefficients by Means of Monte-Carlo Simulation on Photo Activation Analysis of the Samples Irradiated in Nonuniform Bremsstrahlung Field of Microtron", Jul. 24, 2011, J. Radioanal. Nucl. Chem. (291), pp. 497-501. [DOI 10.1007/s10967-011-1324-3].*

(Continued)

Primary Examiner — Anastasia Midkiff
(74) Attorney, Agent, or Firm — Nixon & Vanderhye P.C.

(57) ABSTRACT

A method to determine a concentration of a target element in a sample is provide. The method comprises (i) positioning a sample containing a target element with respect to a reference material containing a reference element, (ii) simultaneously irradiating the sample and the reference material with Bremsstrahlung X-rays to thereby produce activated nuclei in the target element and to produce activated nuclei in the reference element, (iii) detecting deactivation gamma-rays' from the irradiated sample and deactivation gamma-rays from the irradiated reference material, (iv) determining a first number of detected deactivation gamma-rays from the irradiated sample and a second number of detected deactivation gamma-rays from the reference material, and (v) determining the concentration of the target element in the sample by first normalising the first number of detected deactivation gamma-rays from the irradiated sample by the second number of detected deactivation gamma-rays from the reference material. The variation of the reference element to target element cross section ratio over a range of electron beam energies is less than a predetermined measurement accuracy.

20 Claims, 5 Drawing Sheets

(52) U.S. Cl.
CPC ... *G01N 2223/07* (2013.01); *G01N 2223/072* (2013.01); *G01N 2223/074* (2013.01); *G01N 2223/1016* (2013.01); *G01N 2223/3037* (2013.01)

(56) References Cited

U.S. PATENT DOCUMENTS

| | | | |
|---|---|---|---|
| 6,002,734 A | 12/1999 | Steinman | |
| 6,791,089 B1* | 9/2004 | Caffrey | G01N 23/222 250/358.1 |
| 7,778,783 B2* | 8/2010 | Lingren | G01T 3/06 250/307 |
| 2014/0284490 A1* | 9/2014 | Caffrey | G01N 23/222 250/390.04 |

FOREIGN PATENT DOCUMENTS

| | | |
|---|---|---|
| JP | 2004-219187 A | 8/2004 |
| RU | 2139525 | 10/1999 |
| SU | 464224 A1 | 5/1996 |

OTHER PUBLICATIONS

Hamid, Ashraf, "K0-prompt Gamma Ray Activation Analysis for Estimation of Boron and Cadmium in Aqueous Solutions", Oct. 4, 2011, J. Radioanal. Nucl. Chem. (292), pp. 229-236. [DOI 10.1007/s10967-011-1457-4].*
Grozdov, D.S. et al., "Computation of correction coefficients by means of Monte-Carlo simulation on photo activation analysis of the samples irradiated in nonuniform bremsstrahlung field of microtron," Journal of Radio-analytical and nuclear chemistry, 291(2), pp. 497-501, DOI: 10.1007/s10967-011-1324-3 (2012).
Bourmistenko, "Gamma-activation installation for fast determination of gold and its accompanying elements in ore samples," Isotopenpraxis Isotopes in Environmental and Health Studies, 1981, vol. 17, No. 6, pp. 241-243.
International Search Report for PCT/AU2014/050424, mailed May 26, 2015, 4 pages.
Written Opinion of the ISA for PCT/AU2014/050424, mailed May 26, 2015, 6 pages.
Bourmistenko, "Gamma-activation installation for fast determination of gold and its accompanying elements in ore samples,", Isotopenpraxis Isotopes in Environmental and Health Studies, 1981, vol. 17, No. 6, pp. 241-243.
International Preliminary Report on Patentability and Written Opinion in Application No. PCT/AU2014/050424 issued Jun. 21, 2016.

* cited by examiner

METHOD FOR RAPID ANALYSIS OF GOLD

This application is the U.S. national phase of International Application No. PCT/AU2014/050424 filed 16 Dec. 2014, which designated the U.S. and claims priority to GB Patent Application No. 1322365.6 filed 18 Dec. 2013, the entire contents of each of which are hereby incorporated by reference.

TECHNICAL FIELD

The present invention relates to an improved method to determine a concentration of a target element in a sample. In a particular example an improved method to determine the concentration of gold in a sample is provided.

BACKGROUND

In the process of exploration and exploitation of mineral deposits, notably gold and platinum group metal deposits, ore sampling is a specifically difficult problem because such elements in nature are distributed extremely irregularly and their respective quantities are very small. Hence, an analytical method is required to be capable of determining such elements in sufficiently large samples with a high sensitivity.

Fire assay has been the industry standard for the majority of mineral deposit evaluations and has been the method of choice for gold analysis. However the procedure requires complicated sample preparation, is very labour intensive as most steps in the method occur in crucibles and cupels and involves extremely high temperatures (~1100° C.). Furthermore, the analysis is typically performed in an offsite laboratory. Rapid results by this technique are therefore not possible. Furthermore, the small mass of sample analysed, typically 20-50 g, can introduce significant sampling errors for inhomogeneous ore samples. Furthermore, the original sample is destroyed in the process, preventing subsequent reanalysis.

An alternative method for the analysis of elements in mineral ores, including gold, is the gamma-activation analysis method (GAA), GAA is based on sample activation by highly energetic gamma-rays. The GAA method involves irradiating samples with an accelerator producing high energy Bremsstrahlung X-rays.

For the analysis of gold, X-rays having an end-point energy of around 8 MeV are optimal. These will activate any gold in the sample and the activated gold-nuclei decay to produce a 279 keV gamma-ray. A detector then counts the gamma-rays produced. For the measurement of the platinum group metals and many other elements, a higher X-ray end-point energy is required, typically in the range 11-14 MeV. Each element produces one or more gamma-rays of characteristic energy by which it may be identified and quantified.

There is a direct relationship between the gamma-ray strength and the quantity of the target element, which allows the elemental content of the sample to be determined. However, to accurately determine the elemental content of the sample requires accurate knowledge of the intensity and the energy spectrum of the X-ray source, which is highly susceptible to factors such as temperature variations within the accelerator.

For example, variations of a few hundred keV about a nominal X-ray end-point energy of 8 MeV can change the activation yield for gold by tens of percent. If uncorrected, this would lead to correspondingly large errors in the estimated gold content of the samples.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

In one aspect, a method to determine a concentration of a target element in a sample is provided, the method comprising:

positioning a sample containing a target element with respect to a reference material containing a reference element;

simultaneously irradiating the sample and the reference material with Bremsstrahlung X-rays to thereby produce activated nuclei in the target element and to produce activated nuclei in the reference element;

detecting deactivation gamma-rays from the irradiated sample and deactivation gamma-rays from the irradiated reference material;

determining a first number of detected deactivation gamma-rays from the irradiated sample and a second number of detected deactivation gamma-rays from the reference material; and determining the concentration of the target element in the sample by first normalising the first number of detected deactivation gamma-rays from the irradiated sample by the second number of detected deactivation gamma-rays from the reference material;

wherein the variation of the reference element to target element cross section ratio over a range of electron beam energies is less than a predetermined measurement accuracy.

With regards to the predetermined measurement accuracy, the accuracy of the results can be optimised by selecting a reference material such that the variation of the reference element to target element cross section ratio over a range of electron beam energies is less than about 3%, preferably less than 2% and more preferably less than about 1%.

The accuracy of the results can be further optimised by selecting a reference material such that the deactivation gamma-rays from the irradiated reference element have a lower energy than the deactivation gamma-rays from the irradiated sample. This will prevent gamma-rays from the reference material that deposit only part of their energy in the detector system from being misidentified as originating from the target element. In an embodiment where the target element is gold, the reference element should produce only gamma rays with energies below 279 keV.

With regards to the use of the term 'lower energy' it should be appreciated that what is meant is that the gamma-rays from the reference element should be readily resolvable from the gamma-rays from the target element, using the gamma-ray detection system.

The accuracy of the results can be further optimised by selecting a reference material such that the reference element has a half-life that is similar or less than the half-life of the target element. This has the advantage of avoiding activation building up in the reference material over multiple cycles.

The half-life of the reference element activation product is preferably greater than the time required by a sample transport system to move the sample material from an irradiation position to a measurement position. Still preferably, the ratio of the half-lives of the reference element activation product and the sample containing the target element's activation product is as close to unity as possible.

The accuracy of the results can be further optimised by selecting a reference material whose natural abundance is rare in the samples to be analysed. The maximum expected mass of the reference element occurring naturally in the samples to be measured may be less than 1 mg.

Still further, the accuracy of the results can be further optimised by selecting a reference material such that the reference element has an activation cross-section such that the mass of the reference element required to give a strong signal is >100 times larger than the mass of the target element that would be expected to occur naturally in the sample. This ensures that >99% of the signal from the reference element comes from the reference material and not from the sample. More preferably the reference element has an activation cross-section such that the mass of the reference element required to give a strong signal is >1000 times larger than the mass of the target element that would be expected to occur naturally in the sample.

The material containing the reference element may be radiation hard, such that it can withstand an X-ray dose corresponding to many measurement cycles without degradation of its physical properties, or loss of the reference element.

In one embodiment the target element is gold and the reference element is bromine (Br). In another embodiment the target element gold, and the reference element is either selenium (Se) or erbium (Er).

In another embodiment, the target element may be one or more of the platinum group metals (Ir, Os, Pd, Pt, Rh or Ru). In still another embodiment, the target element may be any element considered to be of high value, including but not limited to Cu, Zn, Pb, Sn, Ag or Ni.

In embodiment where the target element is gold, the Bremsstrahlung X-rays preferably have an end-point energy of around 8 MeV.

The method may include configuring the shape of the reference material such that it has the form of a disc whose diameter is substantially the same as, or slightly less than, the diameter of the sample material, and whose thickness is small enough to minimially attenuate radiation emitted by the element of interest from the activated sample. The disc may have a thickness of between 0.1 mm and 3.0 mm and a diameter between 50 mm-100 mm. The shape of the sample may have a generally cylindrical shape. The method may further comprise positioning the reference material such that its axis generally aligns with the axis of the sample.

The method may further comprise positioning a first high resolution detector adjacent to an outer face of the reference material and a second high resolution detector adjacent another outer face of the sample.

The step of positioning the sample with respect to a reference material may comprise releasably fixing the sample with respect to a reference material.

In one embodiment each of the first and second high resolution detectors are generally cylindrical and have a diameter substantailly the same as or greater than the diameter of the sample. Each of the first and second high resolution detectors may comprise large area semiconductor devices having a FWHM resolution at 279 keV of 1.5 keV or better.

In some embodiments, the reference material may be selected such that the variation, with sample composition, in the attenuation of the X-rays causing activation in the reference material is lower than the variation in the attenuation of the X-rays causing activation in the sample.

A significant advantage of at least one embodiment of the invention is that the methodology corrects for variations in the power of the X-ray source, and the energy of the X-ray source, both of which are factors which are very difficult to control and therefore result in high measurement errors.

Another advantage of at least one embodiment of the invention is that errors due to variations in the transfer time required to move the sample from an irradiation position to a measurement position is reduced and/or errors due to inaccuracies in positioning the sample during irradiation or measurement are reduced.

It should be noted that any of the various features of each of the above aspects of the invention can be combined as suitable and desired.

BRIEF DESCRIPTION OF THE DRAWINGS

In order that the present invention may be more clearly ascertained, embodiments will now be described, by way of example, with reference to the accompanying drawing, in which.

DETAILED DESCRIPTION

Figure 1:
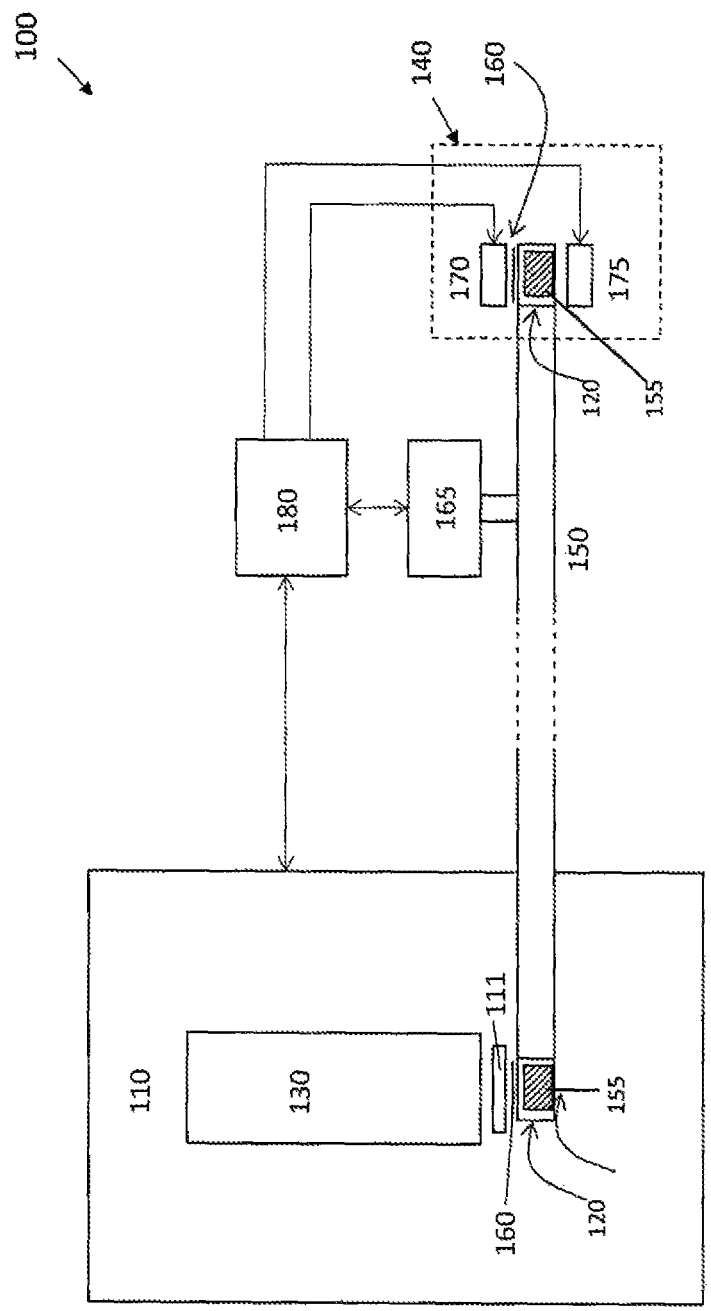
FIG. 1 is a schematic drawing of an apparatus to carry out the methodology of a first embodiment of the invention.

Described embodiments generally relate to an improved method for the analysis of mineral ores, in particular the determination of the concentration of gold in a sample.

A detailed embodiment is disclosed in multiple sections which cover the methodology, the selection of the reference element, and then the apparatus to enable determination of the concentration of the target element, gold, in a sample.

Methodology

The method of gamma-activation analysis relies on being able to accurately relate the measured number of gold-isomer decay gamma-rays $N_{\gamma(Au)}$ back to the gold concentration c of the sample. The equation relating these two values is:

$$N_{\gamma(Au)} = N_{Au} \cdot \varphi \cdot \overline{\sigma}_{Au} \cdot \frac{1}{r} \cdot (1 - e^{-rt_i}) \cdot e^{-rt_e} \cdot (1 - e^{-rt_m}) \cdot p_{\gamma(Au)} \cdot p_{det(Au)} \quad (1)$$

Where:

$N_{\gamma(Au)}$ is the measured number of gold-isomer decay gamma-rays;

$N_{Au}=M_{s\_Au}/m_{Au}$ is the number of gold atoms in the samples, where $M_{s\_Au}$ is the mass of gold in the sample and $m_{Au}$ is the mass of a gold atom;

$\phi$ is the average X-ray flux in the sample (Xrays/cm$^2$/s) from the source;

$\overline{\sigma}_{Au}$ is the average cross-section for producing an excited gold atom, integrated over the normalised energy spectrum of X-rays emitted by the source and attenuated inside the sample;

$t_{1/2}$ is the gold-isomer half-life;

$r=\ln(2)/t_{1/2}$ is the gold decay rate;

$t_i$, $t_c$ and $t_m$ are respectively the irradiation time, the cooling (waiting) time and the collecting measurement time;

$p_{\gamma(Au)}$ is the probability that a decaying gold nucleus emits a 279 keV gamma-ray;

$p_{det(Au)}$ is the probability that an emitted gold gamma-ray will be recorded by the detection system; and c is the concentration of gold in the sample, $c=M_{s\_Au}/M_s$ where $M_s$ is the total mass of the sample.

Any errors in the determination of the parameters appearing in equation (1) will directly lead to inaccuracy in the determination of the concentration c.

The sample mass $M_s$ is able to be determined accurately using conventional weighing equipment. The nuclear parameters m, r, and $p_{\gamma(Au)}$ are well known and available from literature tabulations, specifically, m=196.967 amu=3.27071×10$^{-22}$ g r=log(2)/7.73=0.03894 s$^{-1}$ and $p_{\gamma(Au)}$= 0.709.

The times $t_i$, $t_c$ and $t_m$ can be measured with high accuracy (millisecond precision or better) using a simple electronic timing mechanism linked to the control of the X-ray accelerator and gamma-ray detector. The detection probability $p_{det(Au)}$ is principally a function of the sample size and shape (which are held fixed), the sample mass (which is known), the bulk sample composition (which is unknown, but contributes a relatively small effect) and the positioning of the sample with respect to the detector(s) during measurement.

The detection probability may be estimated using stochastic or analytical computer simulation techniques, such as Monte Carlo modelling. Such techniques may be useful to optimise the design of the sample geometry or gamma-ray detectors. For the purpose of calibration however, accurate knowledge of the gamma-ray detection probability is unnecessary, as any uncertainty is absorbed into a scaling factor (constant of proportionality) determined empirically from measuring the number of activation gamma-rays detected from samples of accurately known gold content.

The major sources of uncertainty relate to the flux and energy spectrum of X-rays from the source, which affect $\phi$ and $\overline{\sigma}_{Au}$. A secondary, minor source of uncertainty is the bulk composition of the sample, which has a small effect on the attenuation of both incident X-rays and emitted gamma-rays.

The proposed methodology corrects completely for variations in $\phi$, corrects very accurately (<1%) for variations in $\overline{\sigma}_{Au}$, and can be used to minimise uncertainties in $p_{au\_det}$, $t_i$, $t_c$ and $t_m$. The proposed methodology also minimises the uncertainty arising from the bulk composition of the sample.

A linear particle accelerator (LINAC) is operable to produce X-rays by accelerating a beam of electrons onto a metal target, which gives rise to Bremsstrahlung radiation. The acceleration of the electrons is achieved by feeding radio-frequency power into an appropriately designed metal cavity. The average electron energy, the spread in energy and the electron beam current can and in general do vary with factors such as the temperature of the accelerator. This in turn changes the number and energy spectrum of X-rays impinging on the sample material.

The excitation of gold in the sample is linearly proportional to the number of X-rays passing through the sample, and varies more strongly (superlinearly) with changes in the X-ray energy. In practice, even small changes in the electron beam energy can produce significant variations in activation yield. For example, variations of a few hundred keV about a nominal beam energy of 8 MeV can change the gold activation yield by an order of tens of percent. This is of course highly undesirable.

The inventors have determined that if a sample of a known reference material is irradiated and measured simultaneously with the gold containing sample, then the reference sample will be activated as well, with the level of activation given by equation (2).

$$N_{\gamma(ref)} = N_{ref} \cdot \varphi \cdot \overline{\sigma}_{ref} \cdot \frac{1}{r} \cdot (1-e^{-rt_i}) \cdot e^{-rt_c} \cdot (1-e^{-rt_m}) \cdot p_{\gamma(ref)} \cdot p_{det(ref)} \quad (2)$$

As will be appreciated, if the reference sample is made from a different element, then the values of the parameters r, $\overline{\sigma}_{ref}$, $p_{\gamma(ref)}$ and $p_{det(ref)}$ will differ for this second element.

If the gold activation signal $N_{\gamma(Au)}$ is normalised by the reference material activation signal $N_{\gamma(Au)}$, then any variation in $\phi$ directly cancels out.

Further, if the reference material is chosen so that the variation in $\overline{\sigma}_{ref}$ with electron beam energy is the same or very similar to the variation in $\overline{\sigma}_{Au}$ with the electron beam energy of gold, then variations in activation resulting from changes in beam energy will also largely cancel. This is a key factor in the selection of the reference element. Additionally, if the reference material and its geometry is chosen such that the variation in $\overline{\sigma}_{ref}$ with the composition of the sample (which arises due to attenuation of X-rays in the sample) is the same or very similar to the variation in $\overline{\sigma}_{Au}$ with composition, then variations in activation resulting from changes in the bulk sample composition also largely cancel. This is a secondary factor in the selection of the reference element and its disposition with respect to the sample.

Dividing equation (1) by equation (2) yields:

$$\frac{N_{\gamma(Au)}}{N_{\gamma(ref)}} = \frac{N_{Au}}{N_{ref}} \cdot T \cdot \left[\frac{\overline{\sigma}_{Au}}{\overline{\sigma}_{ref}} \cdot \frac{p_{\gamma(Au)}}{p_{\gamma(ref)}}\right] \cdot \frac{p_{det(Au)}}{p_{det(ref)}} \quad (3)$$

The factor T includes the decay-rate and timing factors appearing in equations (1) and (2), and depends only on accurately known decay rates, and times that are able to be measured. The factors appearing in the square brackets individually depend on the operating parameters of the LINAC (beam energy and beam current) as well as the cross-sections of the activation reactions for the reference element and gold. However as will be seen, the combined factor in square brackets, for an appropriately chosen reference element, can be made almost independent of these factors and so is rendered approximately constant. Finally, the ratio of detection probabilities appearing after the square bracket depends to an excellent approximation only on the mass of the sample; the form of this dependency can be accurately predicted using Monte Carlo or other computer simulation techniques.

Therefore, equation (3) can be rearranged to give the mass of gold in the samples:

$$M_{S\_Au} = N_{Au} \cdot m_{Au} = \frac{N_{\gamma(Au)}}{N_{\gamma(ref)}} \cdot \frac{1}{T} \cdot f(M_S) \cdot k \quad (4)$$

where $f(M_S)$ is a known function of the sample mass that corrects for the difference in attenuation of the reference and gold gamma-rays and k is a constant of proportionality that absorbs the other factors appearing in equation (3). In practice, the value of k can be determined empirically for a given apparatus configuration and reference element by measuring $N_{\gamma(Au)}$ and $N_{\gamma(ref)}$ for a number of samples of accurately known gold content.

Figure 2:
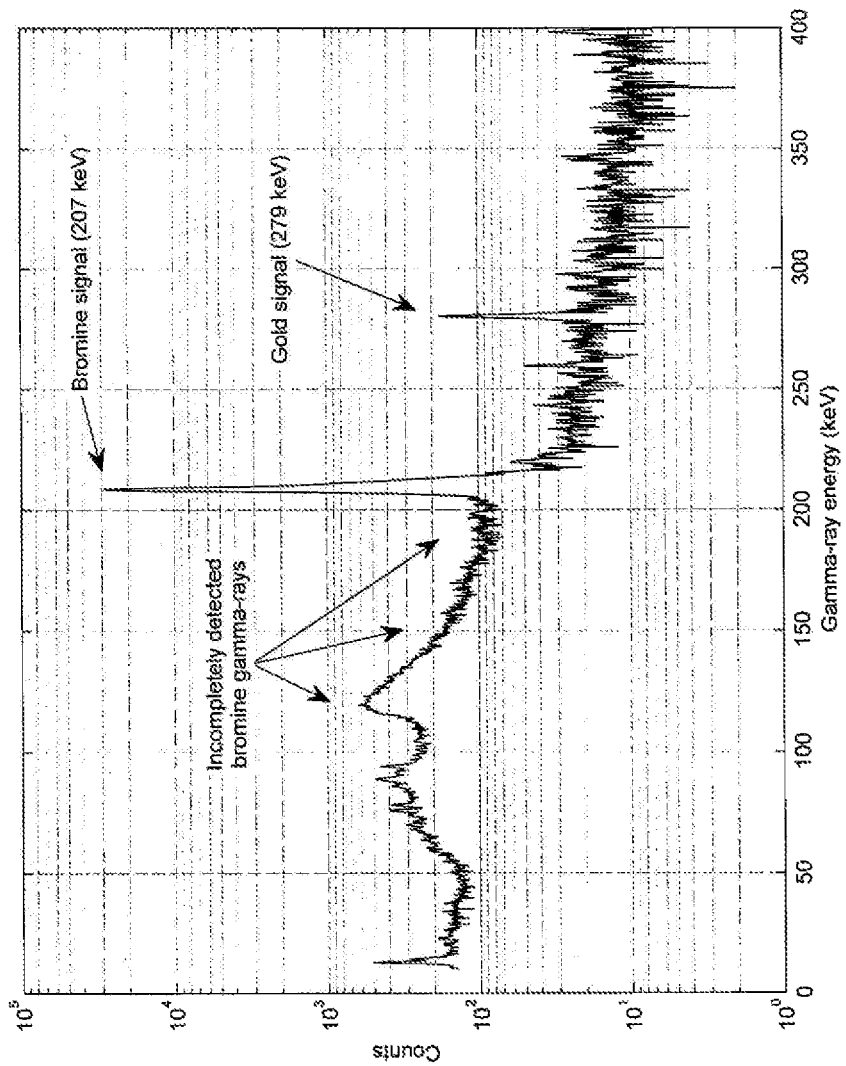
FIG. 2 is a graph of the spectra obtained from gamma-ray analysis of a sample containing gold and a reference material containing bromine.

Additional, secondary factors may be employed in the selection of the reference element. Firstly, it is desirable to produce a strong gamma-ray signal from the reference element to minimise counting statistical error. If the reference element gamma-ray has a higher energy than the gamma-ray emitted from gold, then incompletely detected reference gamma-rays will add to the background beneath the gold peak, reducing the accuracy with which the gold signal can be measured. Therefore, the reference element should produce only gamma-ray(s) with energies below 279 keV, see FIG. 2.

Secondly, the half-life of the reference element may be selected such that it is similar to, or less than that of gold to avoid activation building up in the reference material over multiple measurement cycles. Whilst this could be corrected for, it would be an unnecessary complication. By ensuring that the half-life of the reference material is similar to the half-life of gold, the time factors $t_i$, $t_c$, and $t_m$ appearing in equation (1) are also similar and will largely cancel, reducing the effects of any uncertainty in these parameters, or the decay rate r.

Thirdly and preferably, the reference element should be rare in nature and have an activation cross-section such that the mass of the reference element required to give a strong signal is much larger (>100 times, ideally >1000 times) than the mass of the element that might be expected to occur naturally in the samples. This ensures that >99% (ideally >99.9%) of the signal from the reference element comes from the reference material and not from the sample.

For example, a convenient reference material may contain a few grams of the reference element. If the gold samples to be measured have a typical mass of 500 g, then the concentration of the reference elements occurring naturally in the samples should be below a few tens of parts per million to ensure that the mass of the naturally occurring reference element is below 1% of the mass of the reference element in the reference materials, or below a few parts per million to ensure a mass below 0.1% of the mass in the reference material.

Working Example—Selection of the Reference Element

The activation of gold proceeds via an isomeric reaction, in which stable gold nuclei in their ground state are excited to a long-lived, higher energy state via an inelastic interaction with an energetic X-ray. Isomeric reactions generally proceed at lower X-ray energies than the more common particle-emission reactions. The list of elements exhibiting similar isomeric reactions provided the starting place in the search for a suitable reference element. Gold produces a gamma-ray at 279 keV and it has a half-life of 7.73 seconds.

Table 1 lists the possible elements and isotopes with accessible isomeric reactions. The table show the isotope involved, its natural isotopic abundance, the isomer's half-life (in seconds) and the energies of the main gamma-rays that the isomer emits. The last column assesses the suitability of the listed isotopes against the criteria of half-life and gamma-ray emission energy.

TABLE 1

| Isotope | Abundance | Isomer half-life | Main γ rays | Suitable? |
|---|---|---|---|---|
| $^{77}$Se | 7.63 | 17.36 | 162 keV | Yes |
| $^{79}$Br | 50.69 | 4.86 | 207 keV | Yes |
| $^{83}$Kr | 11.49 | 6588 | Weak x-rays only | Unlikely |
| $^{87}$Sr | 7.00 | 10134 | 388 keV | Unlikely |
| $^{93}$Nb | 100.00 | $5.0902 \times 10^8$ | Weak X-rays only | Unlikely |
| $^{103}$Rh | 100.00 | 3366.84 | X-rays only | Unlikely |
| $^{107}$Ag | 51.84 | 44.5 | 93 keV | Yes |
| $^{109}$Ag | 48.16 | 39.6 | 88 keV | Yes |
| $^{111}$Cd | 12.80 | 2910 | 151, 245 keV | Unlikely |
| $^{113}$Cd | 12.22 | $4.45 \times 10^8$ | Weak X-rays only | Unlikely |
| $^{113}$In | 4.29 | 5968.56 | 392 keV | Unlikely |
| $^{115}$In | 95.71 | 16149.6 | 336 keV | Unlikely |
| $^{119}$Sn | 8.59 | $2.532 \times 10^7$ | X-rays only | Unlikely |
| $^{123}$Te | 0.89 | $1.0299 \times 10^7$ | 159 keV | Unlikely |
| $^{125}$Te | 7.07 | 4959360 | X-rays only | Unlikely |
| $^{129}$Xe | 26.40 | 767232 | X-rays only | Unlikely |
| $^{131}$Xe | 21.23 | 1031098 | 164 keV | Unlikely |
| $^{135}$Ba | 6.59 | 103320 | 268 keV | Unlikely |
| $^{137}$Ba | 11.23 | 153.12 | 662 keV | Unlikely |
| $^{167}$Er | 22.87 | 2.269 | 208 keV | Yes |
| $^{176}$Yb | 12.76 | 11.4 | 190, 293 and 389 keV | Unlikely |
| $^{176}$Lu | 2.59 | 13190.4 | 88 keV | Unlikely |
| $^{177}$Hf | 18.60 | 3084 | 277, 295, 311 and 327 keV | Unlikely |
| $^{177}$Hf | 18.60 | 1.09 | 208, 228 and 378 keV | Unlikely |
| $^{178}$Hf | 27.28 | $9.783 \times 10^8$ | 213, 325, 426, 495 and 574 keV | Unlikely |
| $^{178}$Hf | 27.28 | 4 | 88.9, 213, 325 and 426 keV | Unlikely |
| $^{179}$Hf | 13.62 | 2164320 | 123, 363 and 453 keV | Unlikely |
| $^{179}$Hf | 13.62 | 18.67 | 214 keV | Yes |
| $^{180}$Hf | 35.08 | 19692 | 215, 332 and 443 keV | Unlikely |
| $^{183}$W | 14.31 | 5.2 | 108 keV | Yes |
| $^{190}$Os | 26.36 | 594 | 187, 361, 502 and 616 keV | Unlikely |
| $^{192}$Os | 40.93 | 5.9 | 206, 302, 453, 485 and 569 keV | Unlikely |
| $^{191}$Ir | 37.30 | 4.94 | 129 keV | Yes |
| $^{193}$Ir | 62.70 | 909792 | Weak X-rays only | Unlikely |
| $^{195}$Pt | 33.83 | 346464 | 99 keV | Unlikely |
| $^{199}$Hg | 16.87 | 2560 | 158 and 374 keV | Unlikely |
| $^{204}$Pb | 1.40 | 4032 | 899 and 911 keV | Unlikely |

The list of most suitable reference elements is reduced to Se, Br, Ag, Er, W, Hf and Ir. Hf is excluded from further consideration because of the existence of multiple isomers, some producing very energetic gamma-rays. Ag and W are not preferred due to the low-energy of the gamma-ray lines and the fact that both elements frequently occur in significant concentrations in gold-bearing ores. Ir is not ideal due to the low-thresohld (<8 MeV) for particle emission reactions leading to products that produce high-energy gamma-ray lines.

Of the remaining elements, Br is determined to be the ideal choice. Activated bromine produces a strong gamma-ray at 207 keV versus 279 keV for gold (see FIG. 2). Therefore, there is no interference of the gold signal caused from the bromine signal. Additionally, the half-life of bromine which is 4.86 sec is less than that of gold (7.73 sec). Furthermore, bromine is relatively rare in the earth's crust and therefore it is unlikely that it will be present in the sample material. Also, the mass of bromine required for a strong signal (approximately 1 g) is much larger than the mass of this element expected to occur in natural samples.

Figure 3:
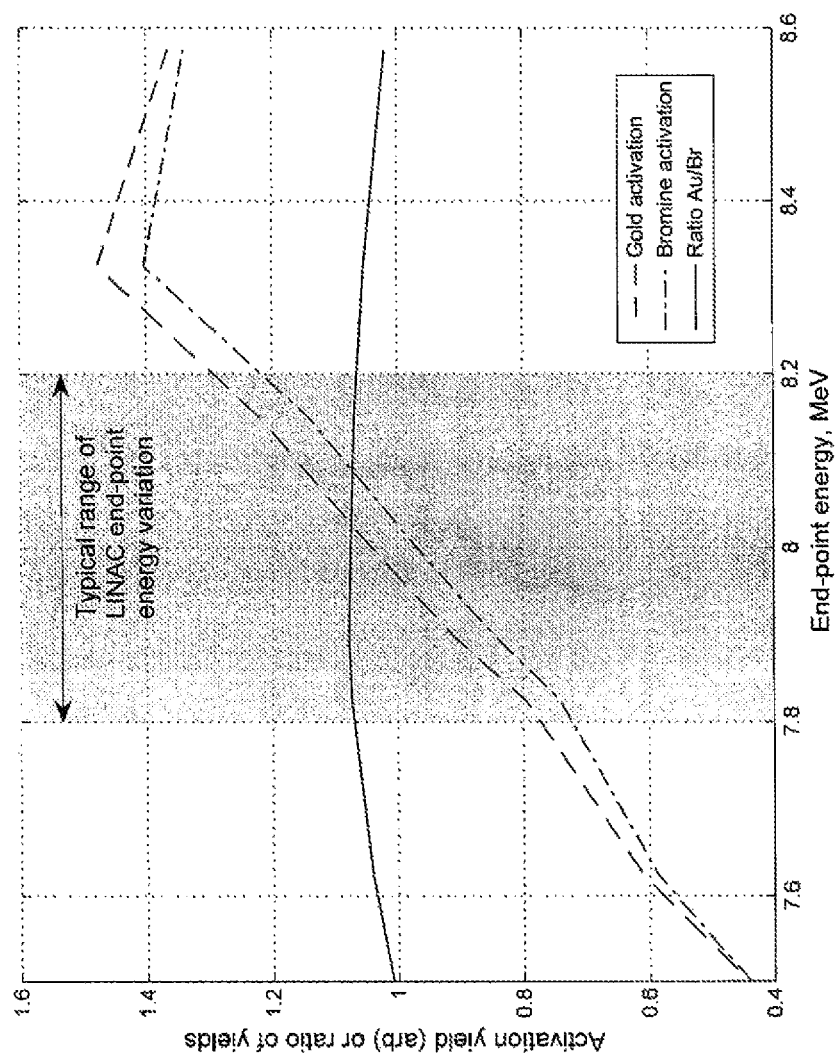
FIG. 3 is a graph showing the activation yield for gold and bromine respectively and the ratio of gold to bromine.

Further, and with reference to FIG. 3, measurements indicate that the ratio of the gold and bromine activation rates shows a broad maximum centred at ~8 MeV electron beam energy, ~8 MeV being the optimal energy to use for activating gold. The variation in the bromine to gold cross-section ratio over a range of electron beam energies likely to be encountered in practice is <1%.

Further, measurements conducted by the inventors demonstrate that for a particular configuration of sample and reference foil, variations in activation of the sample and foil caused by changes in the sample composition also largely cancel, making knowledge of the bulk sample composition unnecessary. However it should be appreciated that the uncertainty due to the composition effect is generally always relatively small (in the worst case of an order of 4%), therefore the effect of the uncertainty due to the composition effect is only important in situations where very high accuracy is desired.

Conveniently, bromine is cheaply available in the form of FR4 printed circuit board substrate, which contains significant levels of bromine-containing compounds. Advantageously, FR4 is radiation hard and mechanically stable. This means that the reference material is able to be reused for an extended period before requiring replacing, thus reducing the frequency at which the apparatus requires recalibrating.

Selenium and erbium are considered as secondary choices for the reference element.

Apparatus

FIG. 1 represents a schematic drawing of an apparatus 100 for the analysis of a gold bearing sample, where the target element is gold. The apparatus includes a sample holder 120 to hold each of the gold bearing samples and the reference material having bromine as the reference element, an irradiation system 130 to irradiate the respective samples, a measurement/detector system 140 to detect and quantify the intensity of characteristic decay products, and a transport system 150 to move the sample holder between the irradiation system 130 and the measurement/detector system 140.

The sample holder 120 is designed to hold the sample 155 and the reference material 160 in a releasably fixed relation with respect to one another, in this example, the reference material 160 has the form of a disc of FR4. The sample holder 120, holding the sample 155 and reference material 160 is operable to be shuttled between the irradiation system 130 and the measurement/detector system 140.

Conveniently, the sample 155 to be measured may be packaged into a cylindrical plastic jar with a screw top. Jars with a volume of about 300 ml are capable of containing up to 500 g of typical gold-bearing ores. The diameter of the jar may be in the range 50-100 mm, and the height of the jar in the range 40-70 mm. Alternatively, the sample may take the form of a cylindrical core-section, with similar dimensions.

The reference material 160 may take the form of a disc or circular sheet, with a thickness of 0.1-3.0 mm, and a diameter substantially similar to the diameter of the jar containing the sample. During irradiation and measurement, the reference material 160 is positioned on one flat face of the sample jar, such that the axis of the reference material 160 coincides with the axis of the jar.

The sample material 155 is irradiated with X-rays through one of its flat surfaces. The irradiation system 130 includes a linear electron accelerator which is substantially enclosed in radiation shielding 110. The linear electron accelerator accelerates a beam of electrons to an energy of ~8 MeV which then impinge on a solid metal target 111 that converts the electrons' energy into X-rays. The electrons are then rapidly slowed down to produce a continuous energy spectrum of X-rays with a maximum energy corresponding to the electron beam energy. The position of the electron beam on the target may be scanned during the process of irradiating the sample, to maximise the uniformity of the X-ray flux passing through the sample container. The sample jar is placed as close as conveniently possible to the outer surface of the X-ray conversion target.

Figure 4:
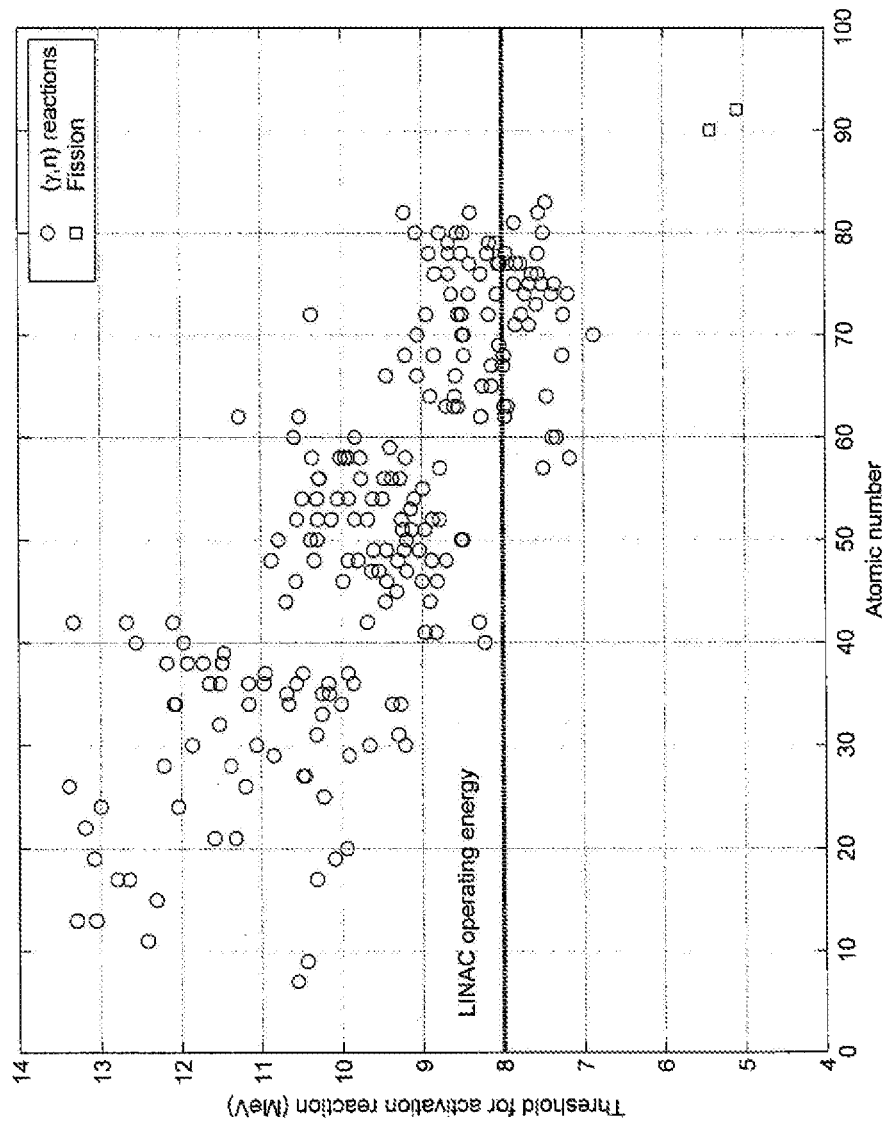
FIG. 4 is a graph showing the activation thresholds for elements having atomic numbers<100.

Advantageously, when gamma-rays have energies less than ~8 MeV, only a small number of elements are activated. The isomeric reactions listed in table 1 may occur, although the natural abundance of most of these elements is low, and the reactions may be readily distinguished from the activation of gold or the reference element from the energies of the gamma-rays that they emit. The thresholds at which neutron-emission reactions leading to radioactive products are plotted as a function of atomic number in FIG. 4. It can readily be seen that the activation thresholds for the major rock forming elements with atomic numbers <30 are significantly above 8 MeV, meaning that these major elements will not be activated. Only high atomic number elements have activation thresholds below 8 MeV, and these elements generally occur at low levels in natural materials. In practice, the largest source of background to the measurement of the gold signal comes from X-ray induced fission of uranium and thorium present in the samples.

This permits the gamma-radiation of the gold isomer to be discriminated against the background of gamma-radiations emitted from other activated elements. Thus the methodology results in high selectivity.

In a preferred embodiment, the reference material 160 is placed on the flat surface of the sample jar facing the target during the irradiation process. A pair of high resolution detectors 170, 175 are used to measure the activation of both the sample 155 and the reference material 160. The respective detectors 170, 175 are cylindrical, preferably of similar or larger diameter than the sample jar, and are placed just far enough apart to admit the sample jar and reference material for measurement. In this example, the detectors 170 and 175 are large-area semiconductor devices, with a FWHM resolution at 279 keV of 1.5 keV or better. It should be appreciated that other detectors as known to those skilled in the art could be used, including but not limited to scintillation detectors.

Measurement of the strength of the signal from the reference material, in the adjacent detector 170 provides a direct measurement of $N_{\gamma(Ref)}$ needed in equation (4). Measurement of the strength of the signal from the reference material in the opposing detector 175 provides a measure of gamma-ray attenuation in the sample, which to supplement, or in place of, a direct measurement of the mass of the sample required to determine the value of $f(M_S)$ in equation (4).

In a second embodiment (not illustrated), the reference material is placed on the flat surface of the sample jar opposite from the target during irradiation. A single detector is used to measure the activation of the sample and the reference material. During measurement, the sample is positioned with respect to the detector so that the reference material is immediately adjacent to the detector. In the second embodiment, it is necessary to correct for attenuation of the primary X-ray beam before it reaches the reference material. This attenuation correction is small, depends primarily on the sample mass, and can be estimated using a Monte Carlo or other computer code in a similar way to the calculation of the function $f(M_S)$ appearing in equation (4).

There is a small dependence of the attenuation correction on the sample composition. In particular, samples such as copper concentrate that contain large concentrations of heavy elements such as iron and copper, attenuate the high-energy X-rays responsible for nuclear activation more strongly than light, rock-forming elements such as silicon and aluminium. This dependence on sample composition could introduce an unwanted calibration bias.

However, with the reference material positioned on the face of the sample opposite from the target, X-rays activating nuclei in the reference material must pass through the full thickness of the sample. In contast, X-rays exciting nuclei in the sample must on average pass through only half of the sample thickness. If the reference material is chosen such that the variation, with sample composition, in the attenuation of the X-rays causing activation in said material is lower than the variation, in attenuation of the X-rays causing activation in the sample, then the dependence on sample composition can be made to cancel. In particular, when the element being measured is gold, and the reference element is bromine, then the variation with composition in relative activation rates of the sample and the reference material is found to be less than 0.2% for a wide range of sample compositions, including carbon, silica and high-grade copper concentrate. Advantageously, this means that a single calibration parameter k may be applied to a wide range of different sample types.

In either embodiment, if the diameter of the reference material is substantially similar to or slightly smaller than the diameter of the sample, then normalising the gold gamma-ray count rate to the reference signal also corrects for small displacements of the X-ray beam with respect to the sample (due to variable position of the sample by the transport system, or fluctuations in the operation of the LINAC 130) and for displacements of the sample with respect to the detectors 170, 175 during measurement. Essentially, these displacements produce a similar affect on both signals and so this source of error also largely cancels.

Furthermore, if the position of the reference material is fixed with respect to the sample, then accidental displacment of the sample and reference material with respect to either the target or the detector(s) reduces the activation of both the reference material and the gold in the sample proportionally. However, as equation (4) determines the gold content from a ratio of the activation levels, this reduction in activation largely cancels. In this way, the analysis is made relatively more insensitive to inaccuracy in positioning of the sample, improving accuracy and reducing requirements on the precision of the sample transport system.

When the sample material and reference material has been irradiated for a sufficient length of time, the irradiation system is turned off. The sample holder 120 is then rapidly moved by means of the transport system 150 to the detector system 140 for analysis. The transport system 150 is operated under control of a control system 165 which in turn is under control by means of a computer 180 which is also responsible for controlling the operation of the accelerator and the gamma-ray detectors 170, 175.

To achieve maximum sensitivity, it is convenient to measure samples for multiple cycles. Advantageously, the number of cycles is chosen to be an even number, and the orientation of the sample jar is flipped 180° between alternate cycles. Unavoidably, the X-ray flux on the surface of the sample closest to the target is higher than the flux on the far side of the sample, and this leads to a higher level of activation. Combining measurements made with the sample in alternate orientations improves accuracy by improving the uniformity of the measurement with respect to the distribution of gold within the sample.

The measurement, irradiation and cooling times should be chosen to give the maximum possible accuracy in a given time. Straightforward analysis shows that this is achieved when the irradiation and measurement times are equal, and the cooling time is as short as possible. Further, the accuracy shows a broad maximum when the measurement and cooling times are equal to 2-3 times the half-life of the sample isotope. For gold, it is convenient to irradiate and measure samples for 20 seconds. The cooling time is set by the rate at which samples can be mechanically transferred from the irradiation to measurement positions. Using a pneumatic or mechanical automated transfer mechanism, this time may be reduced to 2.5 seconds or less.

In summary, the proposed methodology ensures that uncertainties in the parameters appearing in equation (1) can be largely cancelled, by arranging for variations in the LINAC output, energy, sample positioning, timing and sample attenuation to have very similar effects on both the gold and reference gamma-ray signals. Normalising the gold signal to the reference signal causes these similar terms to cancel, significantly reducing measurement uncertainty.

Figure 5B:
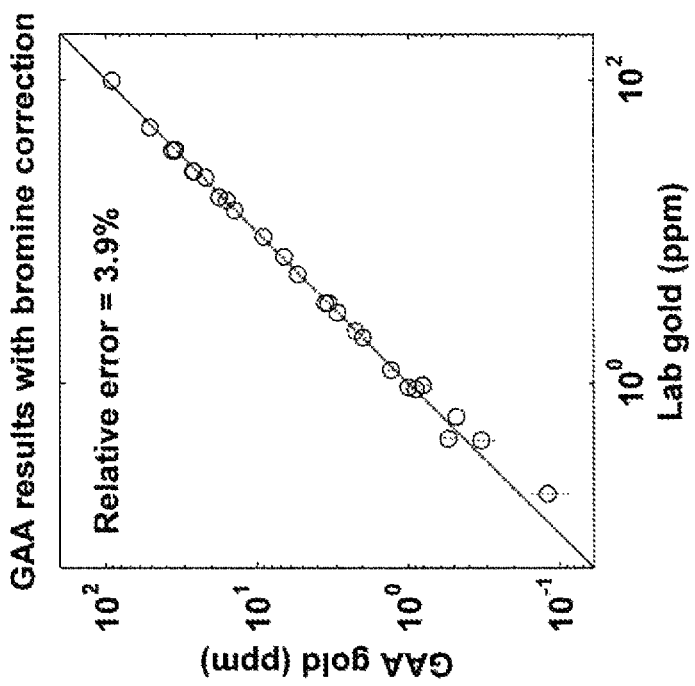
FIG. 5b is a comparative graph showing the gamma-activation analysis results for a gold sample with correction of a bromine reference material.
Figure 5A:
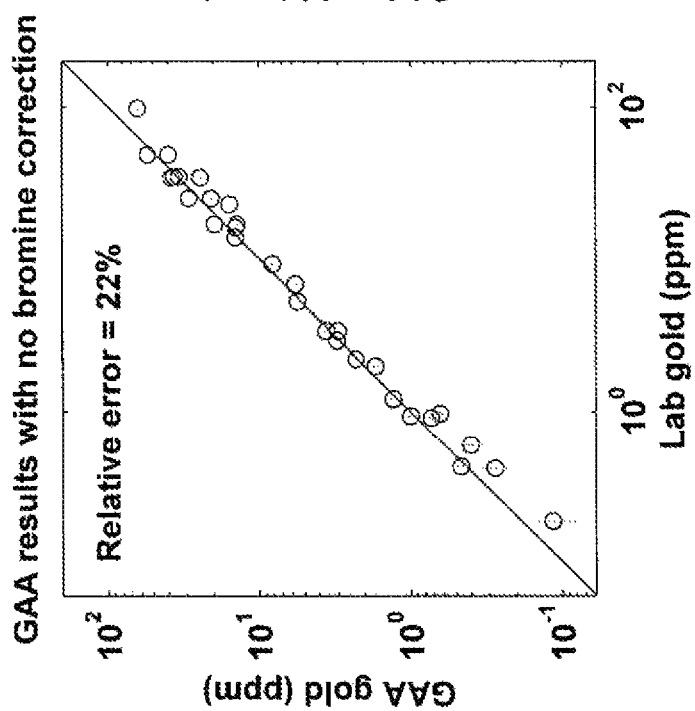
FIG. 5a is a graph showing gamma-activation analysis results for a gold sample without correction of a bromine reference material.

Referring to FIGS. 5a and 5b, it is seen that the use of a bromine reference material standard as described herein affords a substantial improvement in the accuracy of gold analysis possible using GAA. The method allows the impact of fluctuations in the LINAC operating energy or power levels on the determination of the gold level to be reduced below 1%, allowing the gold content of samples to be determined with an accuracy of 3-4% or better.

Furthermore, apparatus calibration is made with respect to standard samples of accurately known gold content. The gold signals of unknown samples are related back directly to these standards via the constant signal from the reference material. It is anticipated that the same reference material would be used for an extended period, limited only be eventual radiation damage and possible loss of Br from the FR4 circuit board. When it is necessary to replace the reference, the system can be recalibrated back to the gold reference material.

In accordance with embodiments of the invention, rapid on-site results are able to be obtained.

It will be appreciated by persons skilled in the art that numerous variations and/or modifications may be made to the above-described embodiments, without departing from the broad general scope of the present disclosure. Whilst in the embodiment described with respect to FIG. 1, the detectors 170 and 175 were described as large-area semi-conductor devices, with a FWHM resolution at 279 keV of at least 1.5 keV, in other embodiments the detectors may be large area scintillation devices. Further, the detectors may have a planar electrode design, with a detector diameter of 80-90 mm or larger, and a thickness of 30 mm or larger.

It is perceived that the invention may also be used to determine the concentration of a platinum group metal in a sample for example or another element considered to be of high value, although the inventors have not ascertained the particular combination of reference element nor the extent of improvement in the accuracy in determination of the concentration of such target elements.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method to determine a concentration of a target element in a sample, the method comprising:
   (i) positioning a sample containing a target element with respect to a reference material containing a reference element, where the target element is distinct from the reference element;
   (ii) simultaneously irradiating the sample and the reference material with Bremsstrahlung X-rays to thereby produce activated nuclei in the target element and to produce activated nuclei in the reference element;
   (iii) detecting deactivation gamma-rays from the irradiated sample and deactivation gamma-rays from the irradiated reference material;
   (iv) determining a first number of detected deactivation gamma-rays from the irradiated sample and a second number of detected deactivation gamma-rays from the reference material; and
   (v) determining the concentration of the target element in the sample by first normalising the first number of detected deactivation gamma-rays from the irradiated sample by the second number of detected deactivation gamma-rays from the reference material;
   (vi) wherein the variation of the reference element to target element cross section ratio over a range of electron beam energies is less than a predetermined measurement accuracy.

2. A method according to claim 1, further comprising selecting the reference material such that the variation of the reference element to target element cross section ratio over a range of electron beam energies is less than 3%.

3. A method according to claim 2, further comprising selecting the reference material such that the variation of the reference element to target element cross section ratio over a range of electron beam energies is less than 1%.

4. A method according to claim 1, wherein the deactivation gamma-rays from the irradiated reference element have a lower energy than the deactivation gamma-rays from the irradiated sample.

5. A method according to claim 1, further comprising selecting the reference material such that the half-life of the reference element is similar or less than the half-life of the target element.

6. A method according to claim 1, wherein the reference element has an activation cross-section such that the mass of the reference element required to give a detectable signal is >100 times larger than the mass of the target element that would be expected to occur naturally in the sample.

7. A method according to claim 6, wherein the reference element has an activation cross-section such that the mass of the reference element required to give a detectable signal is >1000 times larger than the mass of the target element that would be expected to occur naturally in the sample.

8. A method according to claim 1, wherein the target element is gold, and the reference element is bromine (Br).

9. A method according to claim 1, wherein the target element is gold, and the reference element is either selenium (Se) or erbium (Er).

10. A method according to claim 8, wherein the Bremsstrahlung X-rays have an end-point energy of between 7.5 MeV and 8.6 MeV.

11. A method according to claim 1, further comprising configuring the shape of the reference material such that it generally has the form of a disc with a diameter which is substantially the same or slightly less than, the diameter of the sample material.

12. A method according to claim 11, wherein the disc has a thickness of between 0.1 mm and 3.0 mm and a diameter between 50 mm-100 mm.

13. A method according to claim 11, further comprising configuring the shape of the sample such that has a generally cylindrical shape.

14. A method according to claim 11, further comprising positioning the reference material such that its axis generally aligns with the axis of the sample.

15. A method according to claim 11, wherein step (iv) of claim 1 includes positioning the reference material and the sample with respect to a first and a second high resolution detector, where the first high resolution detector is immediately adjacent an outer face of the reference material and the second high resolution detector is immediately adjacent an opposite outer face of the sample.

16. A method according to claim 11, wherein step (iv) of claim 1 includes positioning the reference material and the sample with respect to a high resolution detector, where the high resolution detector is immediately adjacent an outer face of the reference material.

17. A method according to claim 15, wherein either the high resolution detector, or each of the first and second high resolution detectors are generally cylindrical having a diameter equal to or greater than the diameter of the sample.

18. A method according to claim 15, wherein either the high resolution detector, or each of the first and second high resolution detectors comprise large area semiconductor devices having a FWHM resolution at 279 keV of 1.5 keV or better.

19. A method according to claim 1, further comprising repeating (ii) to (vi) for a number of cycles where for each cycle the orientation of the sample with respect to the reference material is changed for alternate cycles.

20. A method according to claim 1, further comprising selecting the reference material such that the variation, with sample composition, in the attenuation of the X-rays causing activation in the reference material is lower than the variation in the attenuation of the X-rays causing activation in the sample.

* * * * *